(12) United States Patent
Komuro et al.

(10) Patent No.: US 7,365,213 B2
(45) Date of Patent: Apr. 29, 2008

(54) ORGANOSILICON COMPOUND, ORGANOSILICON RESIN HAVING DIOL, AND PROCESSES FOR PRODUCING THESE

(75) Inventors: Katsuhiko Komuro, Kyomachi Utsunomiya (JP); Hiroshi Suzuki, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 10/589,262

(22) PCT Filed: Feb. 9, 2005

(86) PCT No.: PCT/JP2005/001972

§ 371 (c)(1),
(2), (4) Date: Jan. 11, 2007

(87) PCT Pub. No.: WO2005/077960

PCT Pub. Date: Aug. 25, 2005

(65) Prior Publication Data

US 2007/0173625 A1    Jul. 26, 2007

(30) Foreign Application Priority Data

Feb. 16, 2004  (JP)  ............... 2004-039064
Feb. 16, 2004  (JP)  ............... 2004-039065

(51) Int. Cl.
  *C07D 305/00*  (2006.01)
  *C08G 77/06*  (2006.01)
  *C08F 283/00*  (2006.01)
(52) U.S. Cl. ............... 549/214; 525/474; 528/40
(58) Field of Classification Search ............... None
  See application file for complete search history.

(56) References Cited

U.S. PATENT DOCUMENTS 4,118,540 A    10/1978  Amort et al.

FOREIGN PATENT DOCUMENTS

| JP | 52 84240 | 7/1977 |
|---|---|---|
| JP | 10-87834 | 4/1998 |
| JP | 10-139787 | 5/1998 |
| JP | 10 139787 | 5/1998 |
| JP | 11-116681 | 4/1999 |

*Primary Examiner*—Samuel A. Barts
(74) *Attorney, Agent, or Firm*—Oblon, Spivak, McClelland, Maier & Neustadt, P.C.

(57) ABSTRACT

[Problems] To provide a novel alkoxysilane having a diol protected, an organosilicon resin which has a diol and the composition of which can be easily regulated, and to processes for producing these.
[Means for solving problems] The alkoxysilane is an organosilicon compound represented by the following formula (1). The organosilicon resin having a diol is one obtained by hydrolyzing-condensing this compound with a multifunctional alkoxysilane.

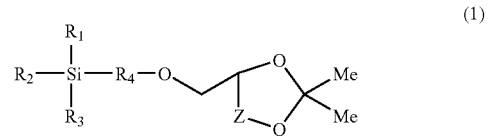

(1)

(In the formula, each of $R_1$, $R_2$ and $R_3$ is an alkyl group or an alkoxy group each having carbon number from 1 to 6. $R_4$ is an alkylene group having carbon number from 2 to 6. Z is an alkylene group having carbon number from 1 to 3.)

The alkoxysilane of the present invention can be produced by a hydrosilylation reaction of a compound represented by the following formula (4) and a silane compound $R_1R_2R_3SiH$.

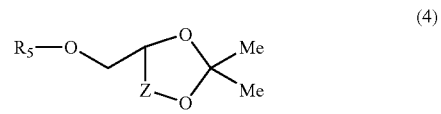

(4)

(In the formula, Z is an alkylene group having carbon number from 1 to 3 and $R_5$ has a carbon-carbon double bond at the terminal.)

The organosilicon resin of the present invention can be produced by a hydrolysis-condensation of a mixture comprising the organosilicon compound represented by the formula (1) above and a molecular weight-controlling agent.

4 Claims, 4 Drawing Sheets

ORGANOSILICON COMPOUND, ORGANOSILICON RESIN HAVING DIOL, AND PROCESSES FOR PRODUCING THESE

TECHNICAL FIELD

The present invention relates to a novel organosilicon compound and a novel organosilicon resin obtained by using this compound as an ingredient. More particularly, it relates to an alkoxysilane having a diol protected by an organic substituent, to an organosilicon resin having a diol and to methods for producing these.

BACKGROUND ART

As one of ingredient compound for producing a poly methyl silsesquioxane-based minute particle having a diol, 3-glycidoxy propyl trialkoxysilane is known (Patent Document 1).

[Patent Document 1] JP-A H11-116681

Additionally, known is a method for synthesizing an organosilicon resin having a diol, in which an alkoxysilane having an alicyclic epoxide is synthesized and hydrolyzed, and an oxidation reaction of the epoxide is conducted.

[Patent Document 2] JP-A H10-87834

A halogenosilane and an alkoxysilane having an alkali-soluble group as typified by diol are useful as an ingredient for a lithography material, an organic-inorganic hybrid material and the like.

There are various types of organosilicon resins having a diol. Known is a method in which an organosilicon resin is previously synthesized and diol is introduced into the resin using polymer reaction. The examples reported are described hereinafter.

Poly methyl silsesquioxane-based minute particle having a diol is reported.

[Patent Document 3] JP-A H11-116681

Moreover, known is a method for synthesizing an organosilicon resin having a diol, in which an alkoxysilane having an alicyclic epoxide is synthesized and hydrolyzed, and an oxidation reaction of the epoxide is conducted.

[Patent Document 4] JP-A H10-87834

According to these methods, it is difficult to accurately control the amount of the diol to be introduced due to use of polymer reaction. And when ingredients are left after the polymer reaction, it is also difficult to remove the remaining ingredients and refine the organosilicon resin. Since an organosilicon resin having a diol shows an excellent alkaline solubility compared with an organosilicon resin having monoalcohol, it is useful as an ingredient for a lithography material, an organic-inorganic hybrid material and the like. In addition, the resin can be an ingredient for a variety of functional materials since the resin is easy to react with a silylating agent.

DISCLOSURE OF THE INVENTION

[Problems to be Solved by the Invention]

According to the previous report, a diol has been introduced into an oraganosilicon resin using polymer reaction. The polymer reaction cannot accurately control the composition of the resin, however, a method for controlling the composition of the resin accurately has been desired. In order to accurately control the composition of the resin, an alkoxysilane having a protected diol is required to be synthesized at high purity and further hydrolyzed for synthesizing the organosilicon resin. An alkoxysilane having a diol protected by an organic substituent has had no examples of synthesis yet.

An object of the present invention is to provide an alkoxysilane having a diol protected by an organic substituent and thereby provide novel methods of synthesis in the fields of organic synthesis and others, a production of a novel resin, a method for treating surface of a material, a modification of resins, and the like.

In case a diol is introduced into an organosilicon resin, as mentioned above, there is only reported that the polymer reaction is used and an accurate control of the composition of the resin was very difficult. In addition, the diol is easy to react with a silanol remaining in the resin, thereby the organosilicon resin having a diol is easy to form a gel.

The other object by the inventors of the present invention is to provide an organosilicon resin having a diol which is stable without time-course changes and a method of producing the same capable of easily controlling the composition.

[Means for Solving Problems]

The present invention relates to an organosilicon compound having a diol protected by an organic substituent, represented by the following general formula (1) and to a method for producing the same.

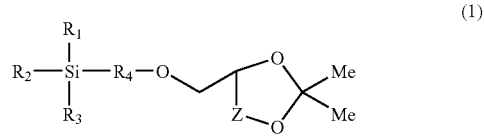

(1)

(In the formula, each of $R_1$, $R_2$ and $R_3$ is an alkyl group or an alkoxy group each having carbon number from 1 to 6, and at least one of $R_1$, $R_2$ and $R_3$ is an alkoxy group. $R_4$ is an alkylene group having carbon number from 2 to 6 and Z is an alkylene group having carbon number from 1 to 3. Me is a methyl group.)

Further, the present invention relates to a method producing organosilicon compounds according to Claim 1 or 2, that is characterized in conducting the following reaction steps A(1) and A(2) sequentially.

Step A(1): A compound represented by the general formula (3) and a halogenated alkene (having the same carbon skeleton as $R_4$ in Claim 1 except that a halogen is bonded to the molecular terminal on the side bonding to O atom and a carbon-carbon double bond is to the molecular terminal on the side bonding to Si atom.) are reacted to a compound represented by the following general formula (4).

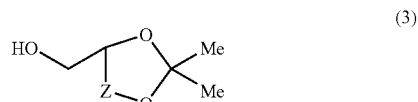

(3)

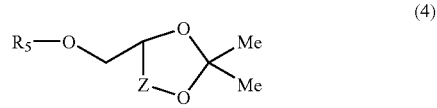

(4)

(In the formula, Z is an alkylene group having carbon number from 1 to 3, and $R_5$ is residue after a halogen is removed of the halogenated alkene and has a carbon-carbon double bond at the terminal.)

Step A(2): The compound represented by the general formula (4) in the Step 1 and a silane compound $R_1R_2R_3SiH$ ($R_1$, $R_2$ and $R_3$ are the same as those in the general formula in Claim 1.) are hydrosilylation-reacted.

The present invention provides an organosilicon resin having a diol which is easy to control the composition and is stable without time-course changes by hydrolyzing an organosilicon compound represented by the following general formula (1).

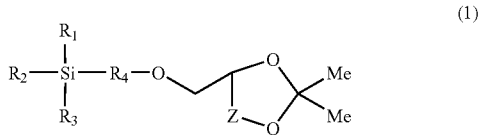

(1)

(In the formula, each of $R_1$, $R_2$ and $R_3$ is an alkyl group or an alkoxy group each having carbon number from 1 to 6, and at least one of $R_1$, $R_2$ and $R_3$ is an alkoxy group. $R_4$ is an alkylene group having carbon number from 2 to 6 and Z is an alkylene group having carbon number from 1 to 3. Me is a methyl group.)

The present invention provides an organosilicon resin having a diol which is easy to control the composition and is stable without time-course changes by hydrolyzing an organosilicon compound represented by the following general formula (2) (hereinafter referred to as "TESDDM"), considering availability and cost of ingredients.

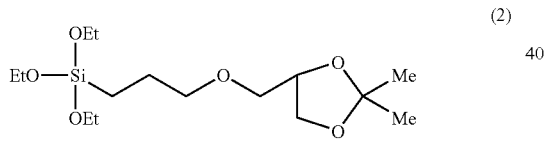

(2)

A method of producing an organosilicon resin of the present invention comprises the following four steps;

Step B(1): An alkoxysilane composition containing an organosilicon compound represented by the general formula (1) and a molecular weight-controlling agent is hydrolyzed and condensed in an organic solvent, further added with an organic solvent, and then is dehydrated with a drying agent.

Step B(2): The drying agent is filtered and then a silylating agent is used to terminate a silanol at the terminal of a resin.

Step B(3): The organic solvent is distilled away and then the organic solvent and water are added to rinse an organosilicon resin having a diol.

Step B(4): A drying agent is used to dry the organosilicon resin and then the organic solvent is distilled away to obtain an organosilicon resin having a diol.

[Effects of the Invention]

According to the present invention, an alkoxysilane having a diol protected by an organic substituent which is a novel organosilicon compound is provided.

The organosilicon compound of the present invention enable a reaction with other organosilicon compound (including polymer) to form a siloxane bond and a coupling reaction with a silanol group in an inorganic compound, since the organosilicon compound has a hydrolyzable alkoxy group which is bonded to silicon atom. In addition, the organosilicon compound is trifunctional alkoxysilane, therefore use of a cross-linking reaction enables constructions of a silicone resin and a silsesquioxane. On the other hand, an organic group with which a hydroxyl group of the diol is substituted is easily desorpted by hydrolysis under an acid condition to form a free diol, which functions as a carbon functional group or an alkali-soluble group. Further the free diol forms a strong hydrogen bond with a polar functional group. It is applied to an organic-inorganic hybrid material utilizing the hydrogen bonding. That is, it functions as a multiple-reactable silicon compound showing a silicon functionality and a protected carbon functionality.

Therefore, the silicon compound of the present invention is useful as an intermediate material for organic synthesis, a starting material for polymer resins, a polymer modifier and a surface-treating agent for inorganic compounds.

According to the present invention, an organosilicon resin having a diol which is easy to control the composition and is stable without time-course changes. Moreover, according to the production method of the present invention, hydrolysis of an alkoxysilane composition containing the organosilicon compound represented by the above general formula (1) leads to an organosilicon resin precursor having a diol. Further a terminal silanol exists in the organosilicon resin precursor immediately after the hydrolysis, and coupling is easily proceded through a desolvation process and a heating process to cause molecule weight changes. Thus dehydration after hydrolysis is conducted, and silanol existing in the organosilicon resin is terminated with a silylating agent. Consequently, rinsing and desolvation are performed to produce a stable organosilicon resin without molecule weight changes.

BEST MODE FOR CARRYING OUT THE INVENTION

First, an organosilicon compound represented by the above general formula (1), that is an alkoxysilane having a diol protected by an organic substituent (hereinafter referred to as "silicon-based compound of the present invention"), will be described in detail hereinafter.

In the present invention, each of $R_1$, $R_2$ and $R_3$ is an alkyl group or an alkoxy group each having carbon number from 1 to 6. Specific examples of $R_1$, $R_2$ and $R_3$ include methyl group, ethyl group, propyl group, butyl group, pentyl group, hexyl group, methoxy group, ethoxy group, propyloxy group, butyloxy group, pentyloxy group and hexyloxy group. These may be in the state of straight chain or branch. Among these, ethoxy group is preferable for $R_1$, $R_2$ and $R_3$ because ingredients are easily available and synthesis is easy.

$R^4$ is an alkylene group having carbon number from 2 to 6 and may be in the state of straight chain or branch. Specific examples include dimethylene group, trimethylene group, tetramethylene group, pentamethylene group, hexamethylene group, 2-methyltrimethylene group and 3-methyltrimethylene group. Among these, straight-chain hydrocarbon having carbon number of 3 is most preferable because ingredients are easily available and synthesis is easy.

Although some specific examples of the silicon-based compound of the present invention may be cited, the most preferable is the compound (hereinafter referred to as "TES-DDM") represented by the following general formula (2) based on the above description.

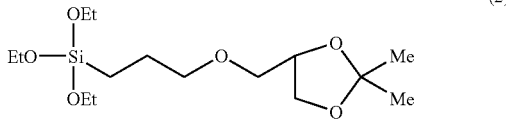

The silicon-based compound of the present invention can be produced, for example, as follows. The compound represented by the following general formula (5) (hereinafter referred to as "DDM") is reacted with an allyl halide in the presence of a base to obtain a compound having a diol protected by an organic substituent, which is represented by the following general formula (6) (hereinafter referred to as "DDMAL").

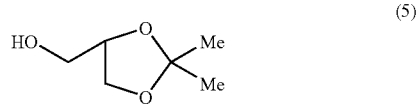

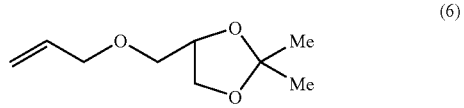

With regard to the reaction, DDM is added with a solvent and a base, and is dropped with an allyl halide while heating and refluxing. Examples of the solvent include alcohols such as methanol, ethanol, isopropanol and butanol; ethers such as diethyl ether, diisopropyl ether and tetrahydrofuran; polar solvents such as water, acetone and dimethylformamide. Examples of the base include sodium hydrate, potassium hydrate, potassium carbonate and the like. Examples of the allyl halide include allyl chloride, allyl bromide, allyl iodide and the like. After completion of the reaction, the solvent and the volatile component are distilled away under reduced pressure and DDMAL is isolated by a reduced-pressure distillation.

Thus obtained DDMAL is reacted with triethoxysilane to obtain TESDDM. This reaction is conducted in the presence of a catalyst. Examples of the catalyst include an elemental metal of group 8 to group 10, such as cobalt, nickel, ruthenium, rhodium, palladium, iridium and platinum, an organic metal complex thereof, a metal salt thereof, a metal oxide thereof, and the like. A platinum-based catalyst is usually used, and examples of the platinum-based catalyst include platinic chloride hexahydrate ($H_2PtCl_6 \cdot 6H_2O$), cis-$PtCl_2(PhCN)_2$, platinum carbon, a platinum complex (Pt-dvds) in which a divinylsiloxane is coordinated, and the like. The symbol "Ph" indicates a phenyl group. The amount of the catalyst used is preferably 0.1 ppm to 1,000 ppm with respect to the total weight of compound represented by DDMAL.

Additionally, a reaction temperature can not be conditionally determined since the operation for controlling the reaction temperature depends on a heating condition from the outside and a charging rate of triethoxysilane. Maintaining a reaction temperature in the range of room temperature to 110° C. usually leads to the hydrosilylation reaction smoothly. After completing the reaction, the solvent and volatile components are distilled away under reduced pressure to obtain the silicon-based compound of the present invention.

Next, an organosilicon resin and a method of manufacturing the same which is easy to control composition and is stable without time-course changes will be described.

The organosilicon compound represented by the above general formula (1) is hydrolyzed and condensed under an acid or a base condition to form the skeleton of an organosilicon resin. When hydrolysis is conducted under an acid condition, the protective group is deprotected to transmit to a free diol. Examples of acid include hydrochloric acid, nitric acid, sulfuric acid, acetic acid, formic acid and the like. Examples of base include sodium hydroxide, potassium hydroxide, lithium hydroxide, tetramethylammonium hydroxide, triethylamine, pyridine and the like. The amount of water used in hydrolysis is equal to or more than the theoretical quantity, and is preferably 1.5 to 2 times the theoretical quantity. Examples of organic solvent used in hydrolysis include acetone, methanol, ethanol, isopropyl alcohol, methylethylketone, methylisobutylketone, propylene glycol monomethyl ether acetate, toluene, hexane and the like. These may be used singly or in combinations of two or more types thereof. Examples of a molecular weight-controlling agent include hexamethyldisiloxane, tetramethyldisiloxane, hexaphenyldisiloxane, hexavinyldisiloxane, tetraphenyldimethyldisiloxane, tetraisopropyldisiloxane and the like. In addition, co-condensation together with trifunctional or tetrafunctionl alkoxysilane such as triethoxysilane, tetraethoxysilane, methyltrimethoxysilane and methyltriethoxysilane may be performed.

Examples of the dehydrating agent using after hydrolysis include anhydrous sodium sulfate, anhydrous magnesium sulfate and the like. And it is not particularly limited so long as it has a dehydration effect and does not contaminate the resin.

The terminal silanol of the resin is terminated with a silylating agent. When the terminal silanol of the resin is terminated, an organosilicon resin having a diol can be synthesized.

Examples of the silylating agent include 1,1,1,3,3,3-hexamethyldisilazane, 1,1,3,3-tetramethyldisilazane, heptamethyldisilazane, 1,3-divinyl-1,1,3,3-tetramethyldisilazane, 1,1,3,3,5,5-hexamethylcyclotrisilazane, tris(trimethylsilyl)amine, bis(diethylamino)dimethylsilane, bis(dimethylamino)dimethylsilane, bis(dimethylamino)diphenylsilane, bis(dimethylamino)methylphenylsilane, trimethylsilanol, t-butylaminotrimethylsilane, and other aminosilanes and silanols; and chlorosilanes such as trimethylchlorosilane, dimethylchlorosilane and phenylmethylchlorosilane. These may also be jointly used with a base such as triethylamine and pyridine.

After the terminal silanol in the resin is terminated, the solvent is distilled away under reduced pressure, and an organic solvent is added, and the organosilicon resin is rinsed. Examples of the organic solvent used in rinsing include acetone, methanol, ethanol, isopropyl alcohol, methylethylketone, methylisobutylketone, propylene glycol monomethyl ether acetate, toluene, hexane and the like. These may be used singly or in combinations of two or more types thereof. Ultrapure water is generally used for rinsing, but it is also possible to use an acid aqueous solution such as aqueous solution of hydrochloric acid, a basic aqueous solution such as aqueous solution of sodium hydroxide, a saturated aqueous solution of sodium chloride, and the like. Rinsing is preferably performed until the water layer becomes neutral.

After rinsing, dehydration and evaporation of the solvent under reduced pressure is performed to obtain an organosilicon resin having a diol which is easy to control the composition and is stable without time-course changes. Examples of a dehydrating agent used after rinsing include anhydrous sodium sulfate, anhydrous magnesium sulfate and the like. Type of the dehydrating agent is not particularly limited insofar as it has dehydrating effects and does not contaminate the resin.

EXAMPLES

Synthesis Example 1

Sodium hydride (10 g: (60% in oil), 250 mmol) was charged into a reaction vessel provided with a condenser, a dropping funnel and a magnetic stirrer. And the sodium hydride was washed with dry hexane. Dimethylformamide (100 mL) was charged into a reaction system and cooled to 0° C. in an ice bath. DDM (30 g, 227 mmol) incorporated into the dropping funnel was dropped slowly. After dropping, stirring is conducted for one hour at room temperature and allyl bromide (30 g, 250 mmol) was slowly added. After the reaction was completed, water (50 mL) and diisopropyl ether (50 mL) were added to wash an organic layer. Anhydrous magnesium sulfate was used for drying and then a transparent and colorless liquid is obtained by distillation under reduced pressure [obtained amount: 21 g, 54%, boiling point: 98-99° C. (at 2,670 Pa)].

When $^1$H-NMR measurement at 270 MHz was performed for this colorless and transparent liquid, the spectrum shown in FIG. 1 was obtained. The d values and identifiers thereof were as shown in Table 1. The compound thus obtained was confirmed as having the structure (DDMAL) shown below.

TABLE 1

| Measurement method | δ (ppm) | Assignment |
|---|---|---|
| $^1$H-NMR | 1.3, 1.4 | a) |
| | 3.4 | b) |
| | 3.7 | c) |
| | 4.0 | d) |
| | 4.2 | e) |
| | 5.2 | f) |
| | 5.9 | g) |

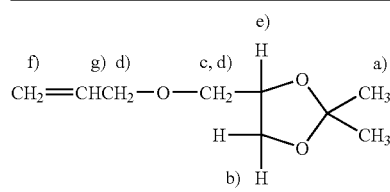

Mass Analysis: MS (CI)=172 (M+H$^+$)

EMBODIMENT 1

DDMAL (20.5 g, 119 mmol) obtained in Synthesis Example 1 was charged into and stirred in a reaction vessel provided with a condenser, a dropping funnel and a magnetic stirrer. Triethoxysilane (21.5 g, 131 mmol) was incorporated into the dropping funnel and 3.8 mL thereof was added into a reaction system. Temperature of an oil bath was set at 80° C. and when the internal temperature exceeded 70° C., a 0.1M Pt-dvds xylene solution (0.02 mL, 0.002 mmol) was placed in to initiate a reaction. After the reaction was completed, a transparent and colorless liquid was obtained [obtained amount: 25 g, 63%, boiling point: 115-116° C. (at 130 Pa)].

When $^1$H-NMR measurement at 270 MHz was performed for this colorless and transparent liquid, the spectrum shown in FIG. 2 was obtained. The d values and identifiers thereof were as shown in Table 2. The compound thus obtained was confirmed as having the structure (TESDDM) shown below.

TABLE 2

| Measurement method | δ (ppm) | Assignment |
|---|---|---|
| $^1$H-NMR | 0.6 | a) |
| | 1.2 | b) |
| | 1.4 | c) |
| | 1.7 | d) |
| | 3.4 | e) |
| | 3.7 | f) |
| | 4.0 | g) |
| | 4.2 | h) |

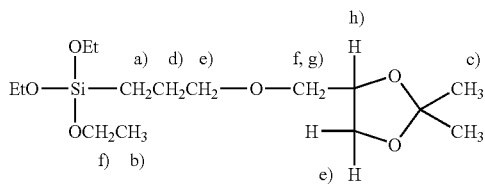

Mass Analysis: MS (EI)=336 (M$^+$)

EMBODIMENT 2

Synthesis of Organosilicon Resin

TESDDM (4.04 g, 12 mmol) obtained in Embodiment 1, methyltriethoxysilane (7.86 g, 44.1 mmol), hexamethyldisiloxane (1.95 g, 12 mmol) and isopropyl alcohol (9.9 g) were charged into and stirred in a reaction vessel provided with a dropping funnel and a magnetic stirrer. An aqueous solution of 1.5 wt % hydrochloric acid (3.74 g) was incorporated into the dropping funnel and slowly dropped. After dropping, stirring was conducted for 1.5 hours at room temperature. Diisopropyl ether (20 g) was added and then anhydrous magnesium sulfate was added and dried for 2 hours. Subsequently the anhydrous magnesium sulfate was filtered and hexamethyldisilazane (3.87 g, 24 mmol) was added slowly while stirring. Stirring was conducted for 2 hours at room temperature, and the solvent is distilled away under reduced pressure. Then methylethylketone (20 g) and 1N-hydrochloric acid solution were added. After washing, and rinsing was repeated until the water layer becomes neutral. Anhydrous magnesium sulfate was used for dehydrating, and the solvent is distilled away under reduced pressure to obtain an organosilicon resin (4.05 g, 57%).

When $^1$H-NMR measurement at 270 MHz was performed for this colorless and transparent liquid, the spectrum shown in FIG. 3 was obtained. The d values and identifiers thereof were as shown in Table 3. It was confirmed that the compound obtained is one having the chemical formula represented by chemical 11 below and as one having the structure represented by chemical 12 below indicating that it is consisted of three types of constituent units shown in chemical 11 below.

$$\left( O_{1.5}Si \diagdown \diagdown \diagdown O \diagdown \diagup^{OH}_{OH} \right)_x$$
$$(SiO_{1.5}-Me)_y \quad (SiO_{0.5}-Me_3)_z$$

(wherein X:Y:Z=15:55:30)

TABLE 3

| Measurement method | δ (ppm) | Assignment |
|---|---|---|
| $^1$H-NMR | 0.1 | a), b) |
|  | 0.6 | c) |
|  | 1.7 | d) |
|  | 3.2-4.0 | e), f), h) |
|  | 4.2 | g) | a)
$$CH_3-\underset{\underset{CH_3}{|}}{\overset{\overset{CH_3}{|}}{Si}}-O-\underset{\underset{O}{|}}{\overset{\overset{CH_3}{|}}{Si}}-O\cdots O-\underset{\underset{O}{|}}{\overset{\overset{CH_3}{|}}{Si}}-O-\underset{\underset{O}{|}}{\overset{\overset{}{|}}{Si}}-CH_3$$
$$\cdots\cdots O-\underset{\underset{O}{|}}{\overset{\overset{CH_3}{|}}{Si}}-O-\underset{\underset{}{|}}{\overset{\overset{}{|}}{Si}}-$$
b)

c) d) e)    f)
—CH$_2$CH$_2$CH$_2$—O—CH$_2$— 
g) H
OH
h) H
OH

When IR was measured, the spectrum shown in FIG. 4 was obtained. The O—H stretching vibration was observed in 3380 cm$^{-1}$ and presence of diol was confirmed.

REFERENCE EXAMPLE 1

Stability Test

Propyleneglycol methyl ether acetate containing 0.5 wt % of water was prepared as a solvent. The organosilicon resin prepared in Embodiment 2 was dissolved in the solvent at a concentration of 10 wt % and was provided as a sample. This sample was left at 60° C. for 3 days and the change in molecular weight was traced. The results are shown in Table 4.

TABLE 4

| No. of days elapsed | Mw | Mn | Mw/Mn |
|---|---|---|---|
| 0 | 1900 | 1400 | 1.3 |
| 1 | 1900 | 1400 | 1.3 |
| 2 | 1900 | 1500 | 1.4 |
| 3 | 1900 | 1400 | 1.3 |

It was confirmed that the organosilicon resin produced by Embodiment 2 was stable, having no change in molecular weight.

INDUSTRIAL APPLICABILITY

It may be useful for lithography.

Figure 1:
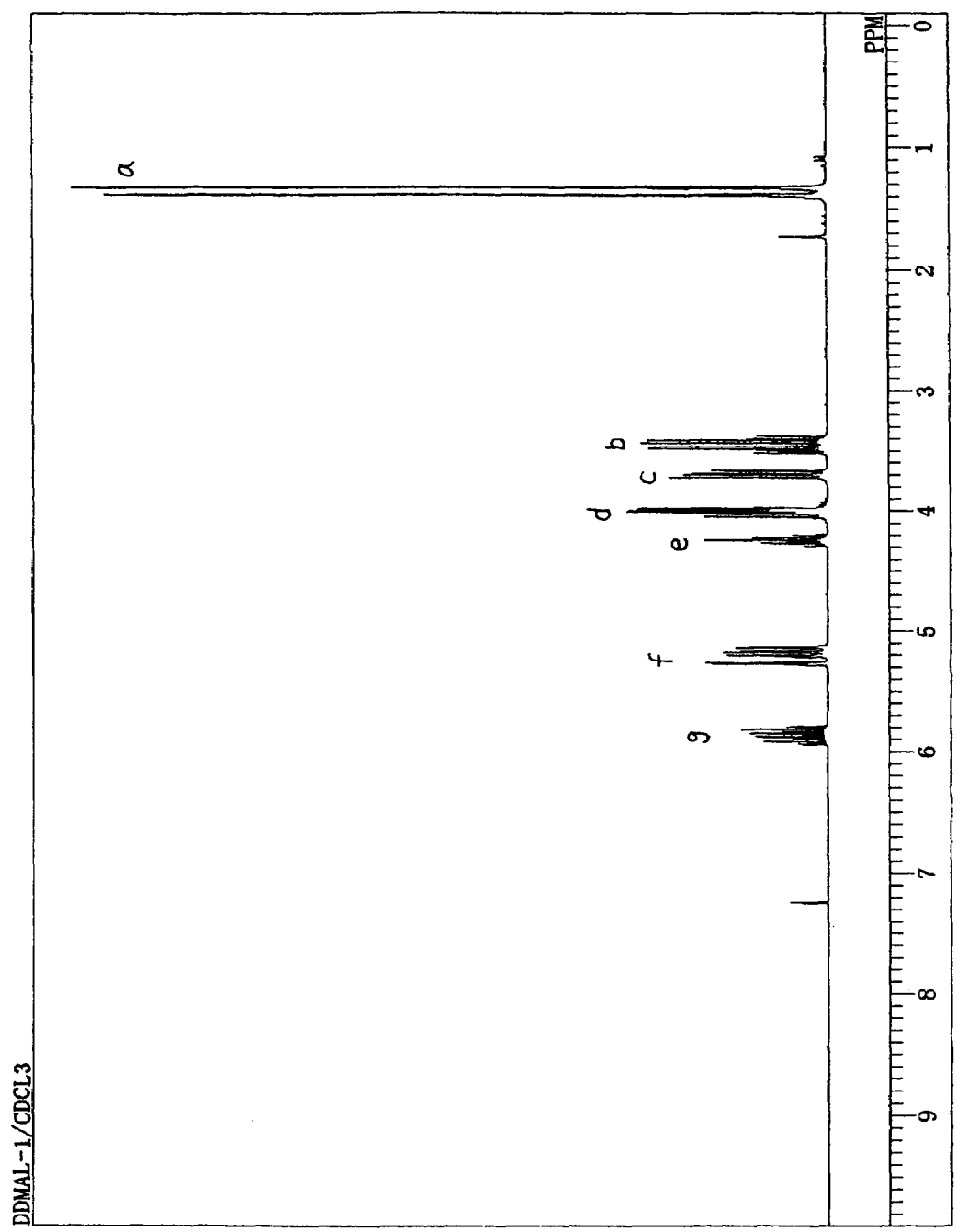
[FIG. 1] is $^1$H-NMR spectrum of the compound obtained in Synthesis Example 1.
Figure 2:
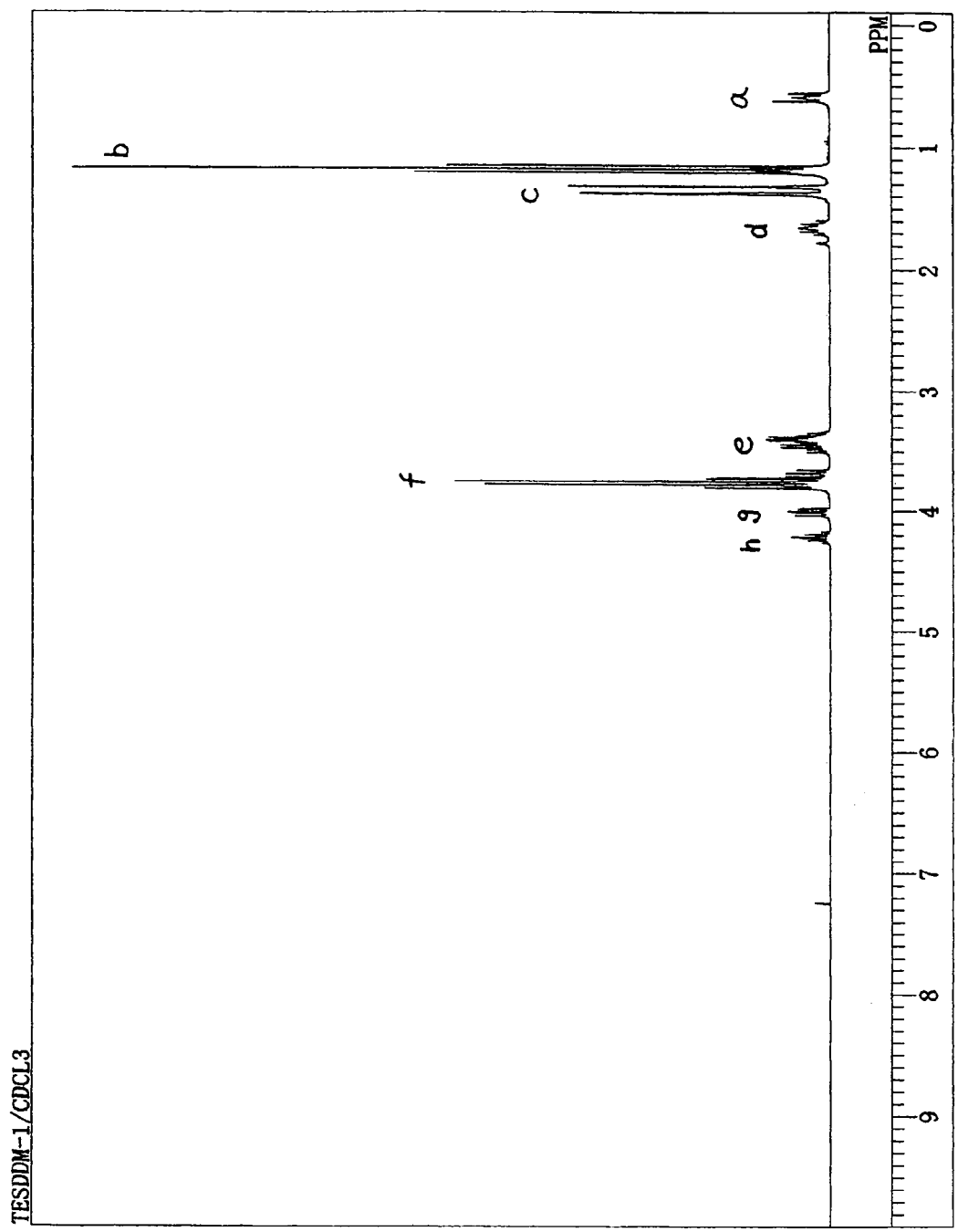
[FIG. 2] is $^1$H-NMR spectrum of the compound obtained in Example 1.
Figure 3:
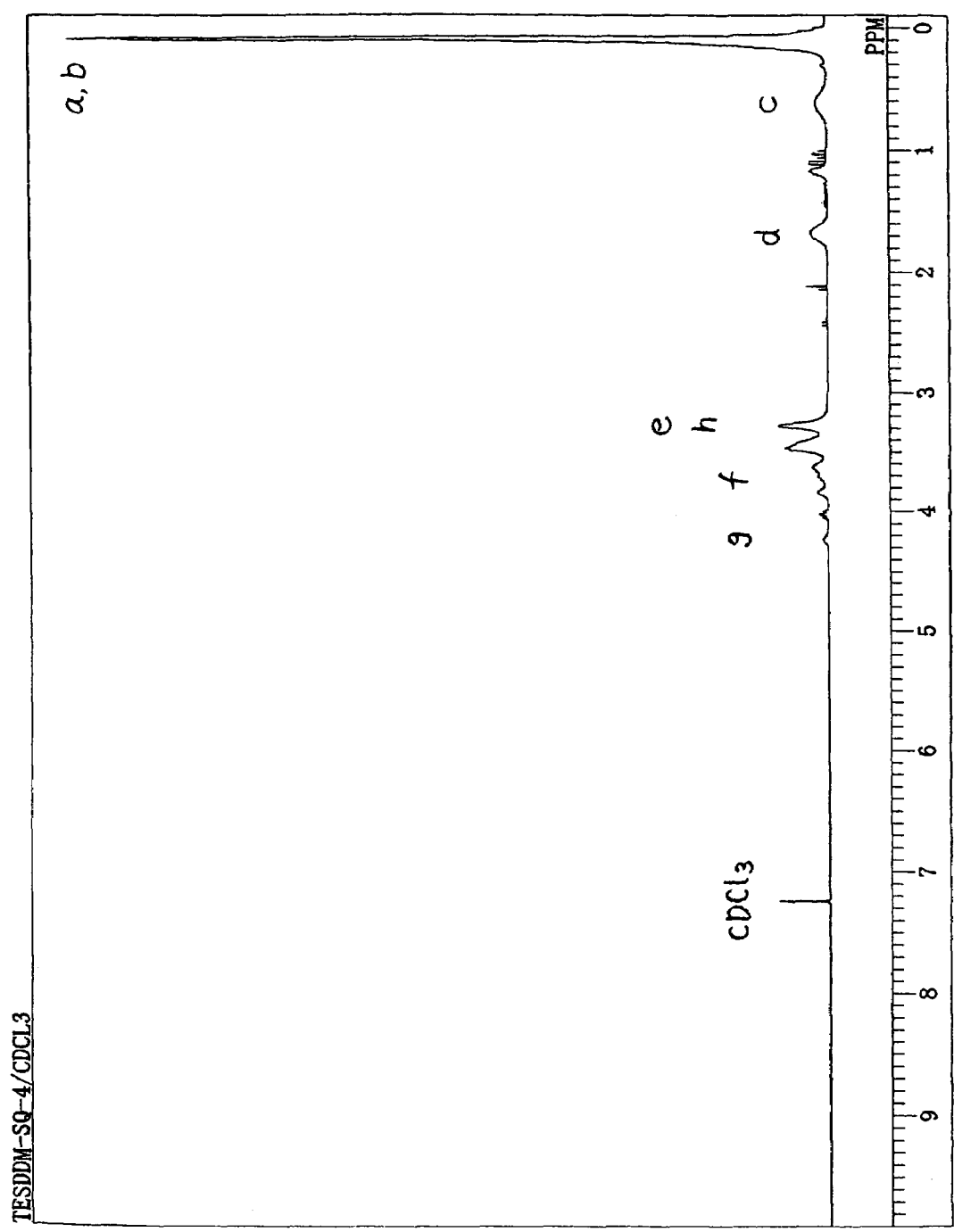
[FIG. 3] is $^1$H-NMR spectrum of the organic silicon resin obtained in Example 2.
Figure 4:
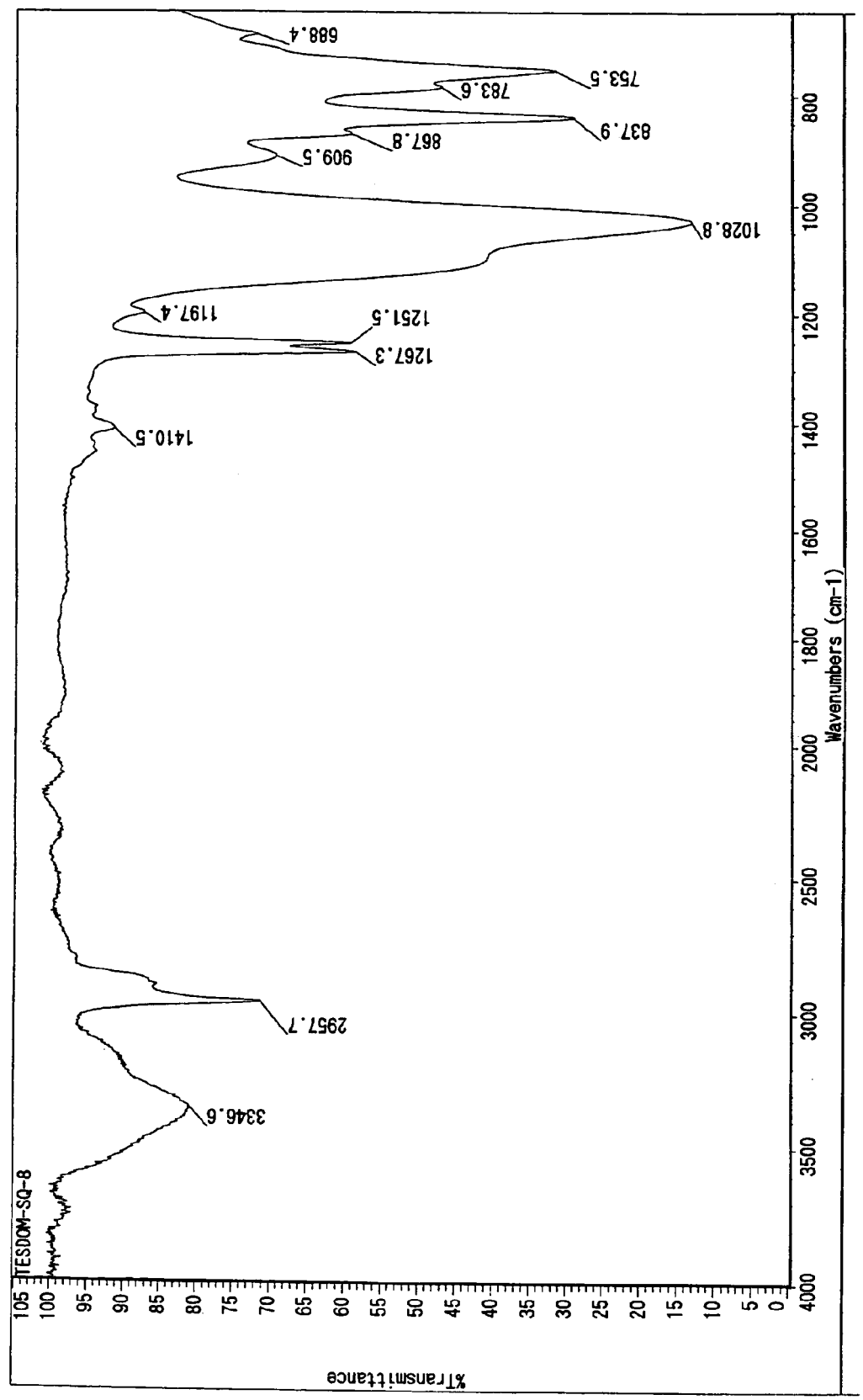
[FIG. 4] is IR spectrum of the organic silicon resin obtained in Example 2.

The invention claimed is:

1. A method for producing an organosilicon compound represented by the general formula (1), characterized in conducting the following reaction steps A(1) and A(2) sequentially:

$$R_2-\underset{\underset{R_3}{|}}{\overset{\overset{R_1}{|}}{Si}}-R_4-O\diagdown\diagup^{O}_{Z-O}\diagup^{Me}_{Me} \quad (1)$$

wherein each of $R_1$, $R_2$ and $R_3$ is an alkyl group or an alkoxy group each having a carbon number of from 1 to 6, and at least one of $R_1$, $R_2$ and $R_3$ is an alkoxy group; $R_4$ is an alkylene group having a carbon number of from 2 to 6; Z is an alkylene group having a carbon number of from 1 to 3 and Me is a methyl group, Step A(1): reacting a compound represented by the general formula (3) and a halogenated alkene having the same carbon skeleton as $R_4$ in formula (1) except that a halogen is bonded to the molecular terminal on the side bonding to the O atom and a carbon-carbon double bond is bonded to the molecular terminal on the side bonding to the Si atom thereby yielding a compound represented by the general formula (4);

$$HO\diagdown\diagup^{O}_{Z-O}\diagup^{Me}_{Me} \quad (3)$$

$$R_5-O\diagdown\diagup^{O}_{Z-O}\diagup^{Me}_{Me} \quad (4)$$

wherein Z is an alkylene group having a carbon number of from 1 to 3; and $R_5$ is the alkene residue after a halogen is removed from said halogenated alkene, said residue retaining a carbon-carbon double bond at its terminal; and Step A(2): hydrosilation-reacting the compound represented by formula (4) in said Step A(1) and a silane compound of the formula $R_1R_2R_3SiH$ wherein $R_1$, $R_2$ and $R_3$ are the same as those in formula (1) to produce the organosilicon compound represented by formula (1).

2. An organosilicon resin having a diol, obtained by hydrolyzing-condensing a cyclic organosilicon compound represented by the general formula (1), or said compound and a multifunctional alkoxysilane

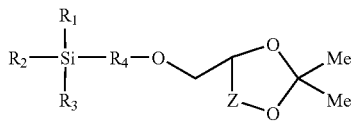

(1)

wherein each of $R_1$, $R_2$ and $R_3$ is an alkyl group or an alkoxy group each having a carbon number of from 1 to 6, and at least one of R1, $R_2$ and $R_3$ being an alkoxy group; $R_4$ is an alkylene group having a carbon number of from 2 to 6; Z is an alkylene group having a carbon number of from 1 to 3; and Me is a methyl group.

3. The organosilicon resin according to claim 2, wherein said organosilicon compound is an organosilicon compound represented by the following general formula (2):

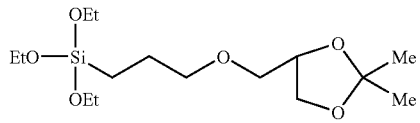

(2)

wherein Et is an ethyl group.

4. A method for producing an organosilicon resin, characterized in conducting the following reaction steps from B(1) to B(4) sequentially:

Step B(1): hydrolyzing and condensing in an organic solvent or in a combination of two or more types of organic solvent an alkoxysilane composition containing a cyclic organosilicon compound represented by the general formula (1) and a molecular weight-controlling agent to form the skeleton of said organosilicon resin and thereafter dehydrating the condensed product with a drying agent;

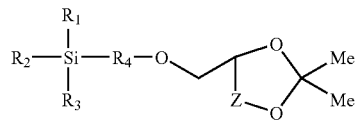

(1)

wherein each of $R_1$, $R_2$ and $R_3$ is an alkyl group or an alkoxy group each having a carbon number of from 1 to 6, and at least one of $R_1$, $R_2$ and $R_3$ being an alkoxy group; $R_4$ is an alkylene group having a carbon number of from 2 to 6; Z is an alkylene group having a carbon number of from 1 to 3; and Me is a methyl group;

Step B(2): filtering the solution of step B(1) to remove said drying agent and thereafter silating the terminal silanol of said condensed product with a silane compound;

Step B(3): distilling away said organic solvent and thereafter rinsing the organosilicon resin with an organic solvent and water; and Step B(4): distilling away said solvent and water of Step B(3) to obtain an organosilicon resin having a diol.

* * * * *